United States Patent [19]

Huffman

[11] 4,056,676

[45] Nov. 1, 1977

[54] HALOGENATED PHENYLTHIOACETAMIDO CEPHALOSPORINS

[75] Inventor: George W. Huffman, Carmel, Ind.

[73] Assignee: Eli Lilly and Company, Indianapolis, Ind.

[21] Appl. No.: 584,998

[22] Filed: June 9, 1975

Related U.S. Application Data

[60] Division of Ser. No. 341,210, March 14, 1973, Pat. No. 3,907,784, which is a continuation-in-part of Ser. No. 288,227, Sept. 11, 1972, abandoned, which is a continuation-in-part of Ser. No. 212,739, Dec. 27, 1971, abandoned.

[51] Int. Cl.$^2$ .................. C07D 501/28; C07D 501/40; A61K 31/545
[52] U.S. Cl. ..................................... 544/29; 424/246; 544/24
[58] Field of Search ................................... 260/243 C

[56] References Cited

U.S. PATENT DOCUMENTS

| | | | |
|---|---|---|---|
| 3,234,222 | 2/1966 | Fechtig et al. | 260/243 C |
| 3,252,973 | 5/1966 | Flynn | 260/239.1 |
| 3,335,136 | 8/1967 | Flynn | 260/243 C |
| 3,507,861 | 4/1970 | Morin et al. | 260/243 C |
| 3,536,698 | 10/1970 | Chauvette et al. | 260/239.1 |

*Primary Examiner*—Nicholas S. Rizzo
*Assistant Examiner*—Diana G. Rivers
*Attorney, Agent, or Firm*—William C. Martens; Everet F. Smith

[57] ABSTRACT

Certain halogenated phenylthioacetamido cephalosporanic acids and derivatives thereof, e.g., 7-[2'-(2",5"-dichlorophenylthio)acetamido]cephalosporanic acid, are effective antibiotics against *Staphylococcus aureus* cultures which show heterogeneous resistance to methicillin.

5 Claims, No Drawings

HALOGENATED PHENYLTHIOACETAMIDO CEPHALOSPORINS

CROSS REFERENCE

This is a division of application Ser. No. 341,210, filed Mar. 14, 1973, now U.S. Pat. No. 3,907,784, which is a continuation-in-part of application Ser. No. 288,227, filed Sept. 11, 1972, and now abandoned, and which is a continuation-in-part of application Ser. No. 212,739, filed Dec. 27, 1971, and now abandoned.

INTRODUCTION

This invention relates to cephalosporin antibiotics and uses of such compounds in therapy against diseases caused by methicillin resistant *Staphylococcus aureus* microorganisms. More particularly this invention provides a method for treating and inhibiting the growth of methicillin resistant Staphylococcus microorganisms with certain halogenated phenylthioacetamidocephalosporanic acids and derivatives thereof. Some of such compounds are new.

BACKGROUND OF THE INVENTION a. Methicillin-Resistant Staphylococcus aureus

Various technical journal articles have been written in the past several years describing the effects or the lack of effectiveness of various antibiotics on various methicillin-resistant cultures of *Staphylococcus aureus*. These cultures have not occurred too often. However, the infections caused by methicillin-resistant strains of *Staphylococcus aureus* are said to be nosocomial in nature in that they appear mostly in bed-ridden or debilitated patients. These pathogenic organisms have been observed in cultures taken from patients with malignancy, chronic bone and/or joint disease, chronically impaired circulation or consciousness, or chronic pulmonary disease.

In addition, bacteriologists have been searching for culture preparation methods for separately identifying methicillin resistant from methicillin susceptible cultures of *Staphylococcus aureus*. They apparently have found at least two in vitro methods, one involving different temperatures of incubation and one involving the use of different sodium chloride concentrations in the culture growth medium, which methods help to distinguish methicillin resistant strains of *Staphylococcus aureus* from those which are not. With these tools the bacteriologists can now more effectively assist and advise clinicians to identify and treat these methicillin-resistant *Staphylococcus aureus* conditions.

b. Cephalosporin Antibiotic History

Cephalosporin C, obtained by fermentation, has been defined as having the following structure:

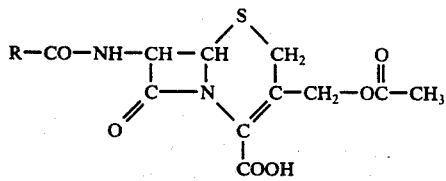

where R is HOOC—CH(NH$_2$)—(CH$_2$)$_3$—. It is also known as 7-(5′-aminoadipamido)cephalosporanic acid. It has weak antibiotic activity, but it is important as a source of cephalosporin C nucleus, i.e., 7-aminocephalosporanic acid (7-ACA), having the structural formula

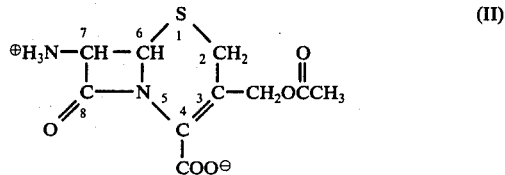

shown here in zwitterionic form, although anionic and cationic salts may be formed and used. Antibiotics such as cephalothin and cephaloridine are prepared from 7-ACA by known methods. Various derivatives of 7-ACA based antibiotics are made by acylating the 7-amino group of 7-ACA with appropriate acyl acids, halides, or other reactive form of such acyl groups and/or by replacing the acetoxy group attached to the 3-methyl carbon atom with appropriate nucleophilic groups now well documented in the literature.

In continued research, desacetoxycephalosporin compounds, i.e., compounds of the structure

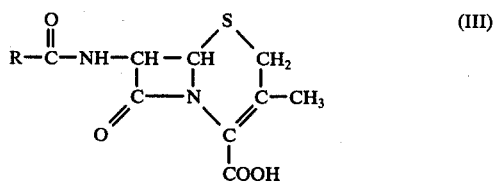

where R is the residue of the acyl group have been prepared. An important known antibiotically active compound in this class is cephalexin, an orally active cephalosporin antibiotic. Morin and Jackson (U.S. Pat. No. 3,275,626) discovered a process for preparing the desacetoxycephalosporanic acid derivatives by rearranging a penicillin sulfoxide ester to the corresponding desacetoxycephalosporin ester, and then removing the ester group. Desacetoxycephalosporanic acid derivative antibiotics are thus obtainable from a penicillin starting material. The compounds are sometimes, for convenience, referred to as being derivatives of 7-aminodesacetoxycephalosporanic acid (7-ADCA) having the structure

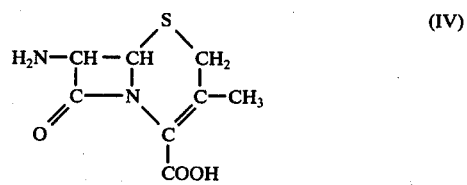

In U.S. Pat. No. 3,335,136, Flynn disclosed and claimed some halophenyl mercaptomethyl cephalosporin compounds which were characterized by penicillinase-resistance, acid stability, and activity against both Gram positive and a number of Gram negative organisms. However, that patent was silent as to the problems of identifying, and methods for treating methicillin-resistant *Staphylococcus aureus* microorganisms. Furthermore, the patent is silent as to the choice of compounds that might be used to treat conditions caused by methicillin-resistant *Staphylococcus aureus* microorganisms.

There is a need for finding the most effective antibiotic compounds for treating methicillin-resistant *Staphylococcus aureus* microorganism and disease conditions caused thereby.

It is an object of this invention to provide a method for treating methicillin-resistant *Staphylococcus aureus* microorganisms with certain polyhalophenylthioacetamidocephalosporin compounds.

It is a more specific object of this invention to provide some specific mono-chloro-, polychloro, and chlorofluoro-phenylthioacetamidocephalosporanic acids, or derivatives thereof as being particularly effective in combatting infections caused by methicillin-resistant *Staphylococcus aureus* microorganisms, some of these compounds being new.

Other objects, aspects and advantages of this invention will become apparent from reading the remaining specification.

SUMMARY OF THE INVENTION

This invention provides a method for treating and inhibiting the growth of methicillin-resistant *Staphylococcus aureus* organisms and disease conditions caused thereby involving treatment of those organisms with certain halophenylthioacetamido cephalosporin derivatives. This invention also provides certain halogenated phenylthioacetamido cephalosporanic acids and derivatives thereof, effective as antibiotics against *Staphylococcus aureus* organisms which exhibit resistance to methicillin. Most of these compounds are useful in depot type parenteral administration procedures. At least one of these compounds, 7-[2'-(3"-chloro-4"-fluorophenyl)thioacetamido]cephalosporanic acid, sodium salt is new, water soluble and is easily administered by intravenous, and intramuscular injection methods.

DETAILED DESCRIPTION OF THE INVENTION

This invention provides an improved method for treating and inhibiting the growth of methicillin-resistant Staphylococcus microorganisms which comprises treating the microorganisms with an effective amount of a compound of the formula

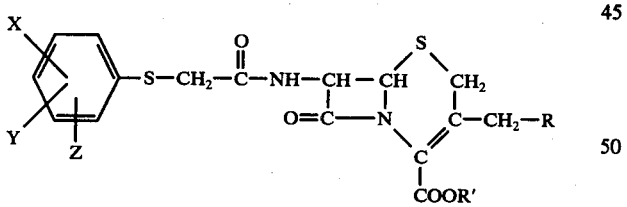

wherein
Z is hydrogen or fluorine; and, when Z is hydrogen, each of X and Y is hydrogen or chlorine selected so that the phenyl ring is substituted with 1 or 2 chlorine atoms and so that when one chlorine atom is present said chlorine atom is in the 3-position, and when two chlorine atoms are present said chlorine atoms are in the 3,4-, the 3,5- or the 2,5-positions; and
when Z is fluorine, said fluorine is in the 3- or 4-position of the phenyl ring, and each of X and Y is hydrogen or chlorine selected so that when the phenyl ring is substituted with 1 or 2 chlorine atoms, one of the chlorine atoms is in the 3- or 4-position of the phenyl ring;

R is selected from the group consisting of
hydrogen,
$C_1$ to $C_4$-alkanoyloxy, e.g., acetoxy,
5-methyl-1,3,4-thiadiazol-2-ylthio,
1-methyl-1H-tetrazol-5-ylthio
1H-tetrazol-5-ylthio
5-phenyl-1,3,4-oxadiazol-2-ylthio,
5-(p-nitrophenyl)-1,3,4-oxadiazol-2-ylthio,
5-(p-methoxyphenyl)-1,3,4-oxadiazol-2-ylthio,
carbamoyloxy [—O C(O)NH$_2$],
methylcarbamoyloxy,
thiomethyl,
N-pyridino,
azido,
dithiocarbamoyl; and
R' is hydrogen, dicyclohexylamine, or a pharmaceutically acceptable cation.

Another aspect of this invention relates to cephalosporin antibiotic compounds of the formula

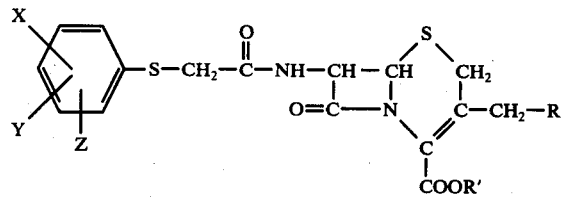

in which
R' is hydrogen, dicyclohexylamine, or a pharmaceutically acceptable cation;
R is selected from the group consisting of hydrogen, $C_1$ to $C_4$-alkanoyloxy, 5-methyl-1,3,4-thiadiazol-2-ylthio, 1-methyl-1H-tetrazol-5-ylthio, 1H-tetrazol-5-ylthio, 5-phenyl-1,3,4-oxadiazol-2-ylthio, 5-(p-nitrophenyl)-1,3,4-oxadiazol-2-ylthio, 5-(p-methoxyphenyl)-1,3,4-oxadiazol-2-ylthio, carbamoyloxy, methylcarbamoyloxy, thiomethyl, N-pyridino, azido, and dithiocarbamoyl;
Z is hydrogen or fluorine; and,
when R is other than $C_1$ to $C_4$-alkanoyloxy, and Z is hydrogen, each of X and Y is hydrogen or chlorine selected so that the phenyl ring is substituted with 1 or 2 chlorine atoms and so that when one chlorine atom is present said chlorine atom is in the 3-position, and when two chlorine atoms are present said chlorine atoms are in the 3,4-, the 3,5-, or the 2,5-positions; and,
when R is other than $C_1$ to $C_4$-alkanoyloxy and Z is fluorine, said fluorine is in the 3- or 4- position of the phenyl ring, and each of X and Y is hydrogen or chlorine selected so that when the phenyl ring is substituted with 1 or 2 chlorine atoms, one of the chlorine atoms is in the 3- or 4- position of the phenyl ring; and,
when R is $C_1$ to $C_4$-alkanoyloxy, and Z is hydrogen, X and Y are chlorine and are in the 3,4-, the 3,5-, or the 2,5- positions; and,
when R is $C_1$ to $C_4$-alkanoyloxy and Z is fluorine, said fluorine is in the 4-position of the phenyl ring, and each of X and Y is hydrogen or chlorine selected so that when the phenyl ring is substituted with 1 or 2 chlorine atoms, one of the chlorine atoms is in the 3-position of the phenyl ring.

The phenyl ring which is delineated by the X, Y and Z substituents includes the following halophenyl moieties: 3-chlorophenyl, 3,4-dichlorophenyl, 3,5- dichlorophenyl, 2,5-dichlorophenyl, 3-fluorophenyl, 4-fluorophenyl, 3-fluoro-4-chlorophenyl, 3-chloro-4-fluorophenyl, 2,4-dichloro-3-fluorophenyl, 3,4-dichloro-5-fluorophenyl, 2,4-dichloro-5-fluorophenyl, 2,4-dichloro-5-fluorophenyl, 3,5-dichloro-4-fluorophenyl, 2,5-dichloro-4-fluorophenyl, and the like.

Besides being characterized by pencillinase resistance, acid stability, and activity against a broad range of Gram positive and a number of Gram negative pathogens, it has been found that the above compounds are highly effective as antibiotics against various methicillin-resistant *Staphylococcus aureus* microorganisms. They are conveniently prepared and administered in the form of the salts of the carboxyl group with pharmaceutically acceptable cations including, for example, sodium, potassium, lithium, ammonium, and substituted ammonium salts such as methylammonium, ethylammonium, as well as the less water soluble salts such as the calcium, barium, procaine, quinine, cyclohexylbis(methylamine) and dibenzylethylenediamine salts. In isolating the compound from its reaction mixture and testing in animals the biscyclohexylamine salts are sometimes used. Administration is preferably by intramuscular injection in sterile water or isotonic saline or dextrose at a dose (for adults) around 0.25 of 0.5 g. every 4 to 6 hours. Oral administration to those compounds which can be absorbed into the blood by this route generally requires a somewhat higher dosage, from 0.50 to 1.0 g. every 4 to 6 hours, and can be accomplished in the form of pressed tablet, filled gelatin capsules, suspensions of conventional type, or the like.

It has been found that most of the compounds of the above described type, examples of which are given below, have antibiotic activity [minimum inhibitory concentration (MIC) values] of less 11 micrograms/milliliter in the absence of human serum in a standard gradient plate testing procedure against methicillin-resistant *Staphylococcus aureus*. The method used is essentially that described by Bryson and Szybalski in 1952 (*Science* 116:45–46). The inoculum treatment method used for penicillin resistant Staphylococci was reported by Godzeski et al in *Antimicrobial Agents and Chemotherapy*, May, 1969, pp. 547–554.

A standard Falcon square plastic petri dish is used. A layer of agar (10 ml.) is poured into one of the square dishes, the dish tipped 5 mm. off the horizontal, and the agar layer allowed to harden in this position. This bottom layer of agar contains the antibiotic, the serum, and/or other material to be tested. The medium is Difco Penassay Agar containing 2 percent agar. We routinely used 4 ml. of human or horse serum for "serum-inactivation" testing. Serum may be added to the top layer also so that no serum gradient will exist, but after testing many antibiotics in this manner no significant differences were noted in the final results between the two types of serum plates. Therefore, serum is routinely added only to the bottom layer.

After the bottom, slanted layer of agar medium has hardened, the plate is placed flat and another 10 ml. of medium added and allowed to harden.

The inoculum of resistant Staphylococci, as described, is prepared by diluting the water suspension 1/50 in 0.25 percent agar in sterile water or saline. For Gram negative organisms, an overnight broth culture is diluted 1/50 in the 0.25 percent agar-water. This dilution is thoroughly shaken to evenly suspend the bacteria. To streak the plate, we use a 1 ml. pipet containing an aliquot of the final 0.05 percent agar dilution. After a little practice, a smooth even stroke of inoculum can be laid down very rapidly. The trick is in the smoothness of the streak—it must be accomplished uniformly and quickly.

After 24 hours incubation at 35–37° C. the plates are ready by simply measuring the length of bacterial growth as a percentage of the entire streak distance which is then converted to the percent of antibiotic concentration in the plate. We have photographically reduced a 100 mm. rule to just fit inside the dish—then the measure in millimeters is equal to the percent concentration.

Average values of duplicate measurements are calculated and the M.I.C.'s reported are averages of 2 streaks on the plate and from 2 to 3 duplicate plates. Eight streaks can be easily placed on each plate. If sharp end points are not obtained, the middle concentration between the beginning of inhibition of the streak to the end of growth is measured. The concentration of the antibiotic under examination is varied from plate to plate in a series as follows:

| 200 | μg/ml. | Plate | No. 1 and 2 |
|-----|--------|-------|-------------|
| 100 | "      | "     | No. 3 and 4 |
| 50  | "      | "     | No. 5 and 6 |
| 20  | "      | "     | No. 7 and 8 |
| 10  | "      | "     | No. 9 and 10 |
| 1   | "      | "     | No. 11 and 12 |

This method of screening pencillins and cephalosporins is quite satisfactory. Control plates containing penicillin and staphcillin or prostaphlin, or other control antibiotic, are used daily for the resistant staphylococcal activity screen. The gradient plate method has shown differences between antibiotics that were not apparent by any other methods of screening. The antibiotic differences, when examined more closely by other methods, e.g., animal therapy, have proved correct. We believe that the gradient plate screen is more sensitive to small differences between related antibiotics than other methods and pictures of the plates can provide a permanent record. The method also lends itself readily to modification of specific purposes—e.g., cross gradients.

The compounds listed below are examples of compounds useful in the method of this invention. After the compound name there is given in parentheses, where tested, the minimum inhibitory concentrations (MIC) in micrograms per milliliter (μg/ml) for the compound in the above described gradient plate procedure test against methicillin-resistant *Staphylococcus aureus*, (in the absence of blood serum/in the presence of 20 percent blood serum).

7-m-Chlorophenylthioacetamidocephalosporanic acid, potassium salt, (2.0/5.2)

7-[2'-(2", 5"-dichlorophenylthio)acetamido]-3-methyl-3-cephem-4-carboxylic acid, 7-[2'-(3",5"-dichlorophenylthio)acetamido]cephalosporanic acid, sodium salt, (2.0/8.7)

7-[2'-(2",4"-dichloro-5"-fluorophenylthio)acetamido]cephalosporanic acid sodium salt, (3.0/>20.0)

7-[2'-(3",4"-dichlorophenylthio)acetamido]cephalosporanic acid, sodium salt, (1.0/1.7)

7-[2'-(2",5"-dichlorophenylthio)acetamido]cephalosporanic acid, sodium salt; (0.8/1.0)

3-carbamyloxymethyl-7-[2'-(2",5"-dichlorophenylthio)acetamido]-3-cephem-4-carboxylic acid (4.1/1.7)

3-[5'-(p-methoxyphenyl)-1',3',4'-oxadiazol-5'-ylthiomethyl]-7-[2'-(2″,5″--dichlorophenylthio)acetamido]-3-cephem-4-carboxylic acid, sodium salt, 4.4/)

3-[5'-(p-nitrophenyl)-1',3',4'-oxadiazol-2'-ylthiomethyl]-7-[2'-(2″,5″-dichlorophenylthio)acetamido]-3-cephem-4-carboxylic acid, sodium salt, (3.9/>20);

3-[5'-phenyl-1',3',4'-oxadiazol-2'-ylthiomethyl]-7-[2'-(2″-5″-dichlorophenylthio)acetamido]-3-cephem-4-carboxylic acid, dicyclohexylamine salt, (0.8/>1);

3-[1'-methyl-1'H-tetrazol-5'-ylthiomethyl]-7-[2'-(3″,5″-dichlorophenylthio)acetamido]-3-cephem-4-carboxylic acid, dicyclohexylamine salt, (2.2/skip zones)

3-(1'H-tetrazol-5'-ylthiomethyl)-7-[2'-(2″,5″-dichlorophenylthio)acetamido]-3-cephem-4-carboxylic acid, dicyclohexylamine salt, (2.3/skip zones);

3-(1'-methyl-1'H-tetrazol-5'-ylthiomethyl)-7-[2'-(3″,4″-dichlorophenylthio)acetamido]-3-cephem-4-carboxylic acid, dicyclohexylamine salt (2.4/>20);

3-(1'-methyl-1'H-tetrazol-5'-ylthiomethyl)-7-[2'-(2″,4″-dichloro-5″-fluorophenylthio)acetamido]-3-cephem-4-carboxylic acid, dicyclohexylamine salt, (1.9/>20)

3-(5'-methyl-1',3',4'-thiadiazol-2'ylthiomethyl)-7-[2'-(3″,5″-dichlorophenylthio)acetamido]-3-cephem-4-carboxylic acid, sodium salt, (4.5/>20)

3-(5'-methyl-1',3',4'-thiadiazol-2'-ylthiomethyl)-7-[2'-(2″,5″-dichlorophenylthio)acetamido]-3-cephem-4-carboxylic acid, sodium salt, (1.8/>1)

3-(5'-methyl-1',3',4'-thiadiazol-2'-ylthiomethyl)-7-[2'-(3″,4″-dichlorophenylthio)acetamido]-3-cephem-4-carboxylic acid, dicyclohexylamine salt, (1.2/>20);

3-(N-methylcarbamyloxymethyl)-7-[2'-(2″,5″-dichlorophenylthio)acetamido]-3-cephem-4-carboxylic acid, (5.5/18.2);

3-(5'-methyl-1',3',4'-thiadiazol-2'-ylthiomethyl)-7-[2'-(2″,4″-dichloro-5″-fluorophenylthio)acetamido]-3-cephem-4-carboxylic acid, sodium salt, (2.3/>20);

3-methylthiomethyl-7-[2'-(2″,5″-dichlorophenylthio)acetamido]-3-cephem-4-carboxylic acid, sodium salt, (12.0/14.4);

7-[2'-(3″-chloro-4″-fluorophenylthio)acetamido]-cephalosporanic acid, (9.3/12.2).

Other useful compounds include:

3-(N-pyridinomethyl)-7-[2'-(2″,5″-dichlorophenylthio)acetamido]-3-cephem-4-carboxylic acid, 3-(N-pyridinomethyl)-7-[2'-(3″-fluoro-4″-chlorophenylthio)-acetamido]-3-cephem-4-carboxylic acid.

3-(N-pyridinomethyl)-7-[2'-(3″,5″-dichlorophenylthio)acetamido]-3-cephem-4-carboxylic acid, 3-azidomethyl-7-[2'-(2″,5″-dichlorophenylthio)acetamido]-3-cephem-4-carboxylic acid, 3-azidomethyl-7-[2'-(3″,4″-dichlorophenylthio)acetamido]-3-cephem-4-carboxylic acid, 3-(aminothiocarbonylthiomethyl)-7-[2'-(2″-5″-dichlorophenylthio)acetamido]-3-cephem-4-carboxylic acid, 3-(aminothiocarbonylthiomethyl)-7-[2'-(2″,5″-dichlorophenylthio)acetamido]-3-cephem-4-carboxylic acid, 3-(1'H-tetrazol-5'-ylthiomethyl)-7-[2'-(2″,5″-dichlorophenylthio)acetamido]-3-cephem-4-carboxylic acid, (6.8/>1), 7-[2'(3″-fluorophenylthio)acetamido]cephalosporanic acid (10.6/9.3), 3-(5'-methyl-1',3',4'-thiadiazol-2'-ylthiomethyl)-7-[2'-(3″-chlorophenylthio)acetamido]-3-cephem-4-carboxylic acid, 3-(1'-methyl-1'H-tetrazol-5'-ylthiomethyl)-7-[2'-(3″-chlorophenylthio)acetamido]-3-cephem-4-carboxylic acid, 3-methylthiomethyl-7-[2'-(3″-fluorophenylthio)acetamido]-3-cephem-4-carboxylic acid, 3-(1'-methyl-1'H-tetrazol-5'-ylthiomethyl)-7-[2'-(4″-fluorophenylthio)acetamido]-3-cephem-4-carboxylic acid, 3-(1'-methyl-1'H-tetrazol-5'-ylthiomethyl)-7-[2'-(3″-chloro-4″-fluorophenylthio)acetamido]-3cephem-4-carboxylic acid, 3-(5'-methyl-1',3',4'-thiadiazol-2'-ylthiomethyl)-7-[2'-(3″-chloro-4″-fluorophenylthio)acetamido]-3-cephem-4-carboxylic acid, 3-(1'-methyl-1'-H-tetrazol-5'-ylthiomethyl)-7-[2'-(3″-fluoro-4″-chlorophenylthio)acetamido]-3-cephem-4-carboxylic acid, 3-(5'-methyl-1',3',4'-thiadiazol-2'-ylthiomethyl)-7-[2'-(3″-fluoro-4″-chlorophenylthio)acetamido]-3-cephem-4-carboxylic acid, 7-[2'-(2″,4″-dichloro-3″-fluorophenylthio)acetamido]-3-methyl-3-cephem-4-carboxylic acid, 3-[5'-(p-methoxyphenyl)-1',3',4'-oxadiazol-5'-ylthiomethyl]-7-[2'-(3″,4″-dichloro-5″-flurorphenylthio)acetamido]-3-cephem-4-carboxylic acid, 3-carbamoyloxymethyl-7-[2'-(3″,5″-dichloro-4″-fluorophenylthio)acetamido]-3-cephem-4carboxylic acid, 3-[5'-phenyl-1',3',4'-oxadiazol-2'-ylthiomethyl]-7-[2'-(2″,5″-dichloro-4″-fluorophenylthio)acetamido]-3-cephem-4-carboxylic acid, and pharmaceutically acceptable salts thereof. The abbreviation "s.z." means skip zones.

The compounds used in the method of this invention can be prepared by methods now known. The starting material for their preparation can be Cephalosporin C, obtained by fermentation. Cephalosporin C can be cleaved by known methods to obtain 7-aminocephalosporanic acid (7-ACA), one of the so-called cephalosporin nuclei. This nucleus (7-ACA) can be converted by acylation of the 7-amino group by known procedures with the acylating agent having the composition which yields the desired 7-acyl side chain. A convenient acylating agent is the appropriate acyl chloride or bromide, or alkyl mixed anhydride, formed in situ. Examples of acylation procedures are given in the detailed examples below. In addition, the various acylation conditions are described e.g., in U.S. Pat. No. 3,335,136.

The selected halophenylthioacetamidocephalosporanic acid can be refluxed with pyridine at 60° C. for 5 hours to form the corresponding 3-(N-pyridinomethyl) compound which can be recovered from the reaction mixture by procedures analogous to those described, for example, in U.S. Pat. Nos. 3,449,338 and 3,577,412. The selected halophenylthioacetamidocephalosporanic acid can be converted to the corresponding 3-azidomethyl-compound by heating an organic solvent solution thereof with sodium azide at a pH of about 7, maintained with a suitable buffer such as disodium phosphate. Similarly, the selected halophenylthioacetamidocephalosporanic acid solution can be heated with sodium dithiocarbamate

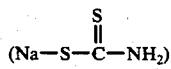

to form the corresponding 3-aminothiocarbonylthiomethyl-compound, by procedures analogous to those found in the literature, e.g., in U.S. Pat. No. 3,573,298.

Compounds having the 3-methyl side chain can be prepared by acylating 7-aminodesacetoxycephalosporanic acid, (7-ADCA) disclosed in U.S. Pat. No. 3,124,576. They can also be prepared by acylating 7-amino desacetoxycephalosporin esters obtained by penicillin sulfoxide ester rearrangement as taught, e.g. in Hatfield U.S. Pat. No. 3,591,585.

The compounds having the thiomethyl, 5-methyl-1,3,4-thiadiazol-2-ylthio, 1-methyl-1H-tetrazol-5-ylthio, 5-phenyl-1,3,4-oxadiazol-2-ylthio, 1H-tetrazol-5-ylthio, 5-(p-nitrophenyl)-1,3,4-oxadiazol-2-ylthio, or 5-(p-methoxyphenyl)-1,3,4-oxadiazol-2-ylthio side chain in the 3-position can be prepared by reacting Cephalosporin C, or 7-aminocephalosporanic acid or ester and N-protected forms of such compounds with the appropriate thiols according to thiolation procedures now known. See, for example, U.S. Pat. Nos. 3,516,996 and 3,530,123. The aminoadipoyl group can be cleaved from Cephalosporin C and the 7-amino group of the thiolated nucleus acid or ester can be acylated as described above. Ester groups are removed by reduction, hydrogenolysis or acid cleavage methods as appropriate for the particular ester group, and salts of the acids are formed, if desired, to assist getting the desired compound out of its reaction mixture, and to increase solubility of the compound in the selected pharmaceutical vehicle, if necessary. Acetoxymethyl esters of the halophenylthioacetamido cephalosporanic acids may be used to enhance absorbability of the compound.

The following detailed examples exemplify procedures for preparing the compounds used in the method of this invention.

EXAMPLE 1

To a solution of 7.1 g (30 mM) of 3,4-dichlorophenylmercaptoacetic acid in 100 ml dry benzene was added 7.5 g (5.0 ml) (60 mM) oxalyl chloride and one drop of DMF. This solution was stirred 3 hrs at 25° C. The benzene was then removed on a rotary evaporator resulting in a yellow syrup which was taken up in benzene and again stripped to removed any residual oxalyl chloride. This syrup was then taken up in acetone (50 ml) and added dropwise over a 1 hr period to a cold solution (−5° C) of 8.5 g of 7-ACA in 200 ml 50% aqueous acetone containing 8.5 g sodium bicarbonate. This mixture was stirred for 2 hrs while slowly warming to 25° C. The acetone was then removed on a rotary evaporator, and the aqueous solution resulting was layered with 100 ml ethyl acetate. Hydrochloric acid was added to pH 2, and the layers mixed and separated. The aqueous phase was re-extracted with two 50 ml portions of ethyl acetate, and the organic phases were combined and dried over magnesium sulfate. The organic solution was filtered and evaporated on a rotary evaporator yielding a clear yellow syrup which was taken up in methanol (250 ml). To this solution was added 30 mM sodium-2-ethyl-hexanoate in 100 ml ethanol. The resulting solution was chilled and reduced in volume to give white crystals of the sodium salt of 7-(3,4-dichlorophenylthioacetamido)cephalosporanic acid. The product had a maximum in its ultraviolet absorption spectrum at 258 m$\mu$ ($\epsilon$=13,400) and exhibited a 1760 cm$^{-1}$ band in its infrared spectrum.

Note: DMF is N,N-dimethylformamide.

EXAMPLE 2

7-(2,5-Dichlorophenylthioacetamido)-cephalosporanic acid was prepared as the sodium salt according to the procedure described in Example 1 and under the same conditions. The product had a maximum in its ultraviolet absorption spectrum at 253 m$\mu$ ($\epsilon$=12,550) and exhibited a 1760 cm$^{-1}$ band in its infrared spectrum.

EXAMPLE 3

7-(3,5-Dichlorophenylthioacetamido)-cephalosporanic acid was prepared as the sodium salt according to the procedure described in Example 1 and under the same conditions. The product had a maximum in its ultraviolet absorption spectrum at 260 m$\mu$ ($\epsilon$=15,600) and exhibited a 1760 cm$^{-1}$ band in its infrared spectrum.

EXAMPLE 4

7-(2,4-Dichloro-5-fluoro-phenylthioacetamido)cephalosporanic acid was obtained as the sodium salt according to the procedure described in Example 1 and under the same conditions. The product had a maximum in its ultraviolet absorption spectrum at 257 m$\mu$ ($\epsilon$=17,500) and exhibited a 1760 cm$^{-1}$ band in its infrared absorption spectrum.

EXAMPLE 5

7-(3,4-Dichlorophenylthioacetamido)cephalosporanic acid sodium salt, 4.34 g., was dissolved in 100 ml aqueous sodium phosphate pH 7 buffer. To this solution was added 1.16 g 1-methyl-5-mercaptotetrazole. This mixture was then heated at 70° C for 4 hrs. The solution was then cooled, layered with ethyl acetate, acidified with HCl to pH 2, and the phases separated. The organic phase was dried over magnesium sulfate, filtered and reduced to a foam. This was taken up in ethanol, and dicyclohexylamine added whereupon the product crystallized as the dicyclohexylammonium salt. The product of 7-[2-(3,4-dichlorophenylthio)acetamido]-3-(1-methyltetrazol-5-yl-thiomethyl)-3-cephem-4-carboxylic acid, had a maximum in its ultraviolet absorption spectrum at 260 m$\mu$ ($\epsilon$=11,600) and exhibited a 1760 cm$^{-1}$ band in its infrared spectrum.

EXAMPLE 6

Following the procedure outlined in Example 5, 3.8 g of 2,5-dichlorophenylthioacetamido cephalosporanic acid as sodium salt and 1.1 g 5-methyl-1,3,4-thiadiazole-2-thiol were dissolved in 100 ml aqueous pH 7 phosphate buffer and heated at 70° C for 4 hrs. The solution was cooled, layered with ethyl acetate, and HCl added to adjust to pH 2. The organic layer was separated, dried over magnesium sulfate, and reduced to a gum. This gum was taken up in ethanol and the product, 7-[2-(2,5-dichlorophenylthio)acetamido]-3-(5-methyl-1,3,4-thiadiazole-2-yl-thiomethyl)-3-cephem-4-carboxylic acid, subsequently crystallized as the acid upon standing. The product had a maximum in its ultraviolet absorption spectra at 254 m$\mu$ ($\epsilon$=15,200) and exhibited a 1700 cm$^{-1}$ band in its infrared spectrum.

EXAMPLE 7

571 mg 2,5-dichlorophenylthioacetic acid was dissolved in 75 ml methylene chloride, and to this solution was added 0.31 ml oxalyl chloride and 2 drops DMF while the temperature was kept at 0° for 5° C for 1 hr. The solution was reduced in volume on a rotary evaporator and subsequently taken up in 15 ml acetone. 546 mg 7-Amino-3-(N-methylcarbamoyloxymethyl) -Δ³-cephalosporanic acid was dissolved in 20 ml water containing 605 mg NaHCO₃. Upon solution 5 ml aceinocula were diluted to 10³ bacteria per spot. Cultures 3055 (benzylpenicillin sensitive) and H232 (benzylpenicillin-resistant) are controls. The remaining cultures are methicillin-resistant, and, except for 3136, are clinical isolates. Culture 3136 is a 4th transfer laboratory selected mutant. The results are given in the following table.

AGAR DILUTION MIC
PHENYLTHIOACETYL CEPHALOSPORINS vs METHICILLIN RESISTANT S. aureus
MIC (μg/ml) for *Staphylococcus aureus* cultures[a]

| ANTIBIOTIC | Controls | | | | | | | | | | | | (Seattle) | Kavarmak | |
|---|---|---|---|---|---|---|---|---|---|---|---|---|---|---|---|
|  | 3055 | H232 | 3130 | 3131 | 3132 | 3133 | 3134 | 3135 | 3136 | 3137 | 3138 | 3139 | 966 | 1138501 | S61 |
| Methicillin[b] | 1 | 2 | 8 | 8 | 8 | 8 | 16 | 8 | 8 | >128 | 16 | 8 | 8 | 8 | 8 |
| Cephalothin | <.25 | <.25 | 8 | 1 | 2 | 2 | 8 | 2 | 2 | 64 | 8 | 1 | 1 | 2 | 2 |
| Cephaloridine | <.06 | <.06 | 4 | 1 | 2 | 4 | 8 | 1 | 0.25 | 8 | 8 | 1 | 0.25 | 1 | 4 |
| Example 3 | <.06 | <.06 | 0.5 | 0.5 | 0.25 | 1 | 0.5 | 0.5 | 0.25 | 2 | 2 | 0.5 | 0.25 | 0.5 | 0.5 |
| Example 1 | <.06 | <.06 | 0.5 | 1 | 0.5 | 0.5 | 1 | 0.5 | 0.5 | 2 | 1 | 1 | 0.5 | 0.5 | 0.5 |
| Example 2 | <.06 | <.06 | 0.5 | 0.5 | 0.5 | 1 | 1 | 0.5 | 0.5 | 2 | 1 | 1 | 0.5 | 0.5 | 0.5 |
| Methicillin[c] | 2 | 2 | 128 | 128 | 32 | 128 | 64 | 64 | 64 | >128 | >128 | >128. | 64 | 128 | 128 |
| Cephalothin | <.25 | <.25 | 64 | 32 | 16 | 64 | 64 | 32 | 32 | 128 | 64 | 32 | 32 | 32 | 64 |
| Cephaloridine | 0.25 | <.06 | 8 | 16 | 2 | 16 | 16 | 8 | 16 | 32 | 16 | 4 | 0.25 | 4 | 16 |
| Example 3 | <.06 | <.06 | 1 | 2 | 0.5 | 1 | 1 | 1 | 2 | 4 | 1 | 1 | 0.5 | 2 | 2 |
| Example 1 | <.06 | <.06 | 1 | 1 | 0.25 | 1 | 0.5 | 0.25 | 0.5 | 2 | 0.5 | 0.25 | 0.25 | 0.5 | 1 |
| Example 2 | <.06 | <.06 | 2 | 1 | 0.5 | 2 | 2 | 1 | 1 | 4 | 1 | 0.5 | 0.25 | 1 | 1 |

Footnotes:
[a]Inocula diluted to 10³ bacteria per spot.
[b]Agar medium contains 0.5% sodium chloride.
[c]Agar medium contains 5.0% sodium chloride.

tone was added and the solution was chilled to −5° C. The acid chloride was then added dropwise to the cephalosporin nucleus and stirred 30 min at 0° C. The acetone was removed on a rotary evaporator and the residue taken up in 50 ml H₂O and 100 ml ethyl acetate/acetone. The solution was adjusted to pH 2.5 with HCl and the organic layer separated and dried over sodium sulfate. Reduction of the organic phase on a rotary evaporator resulted in crystallization of the product. The product 7(2,5-dichlorophenylmercaptoacetamido)-3-(N-methylcarbamoyloxymethyl)-Δ³-cephalosporanic acid had a maximum in its ultraviolet absorption spectrum at 256 mμ (ε=13,800) and exhibited a 1760 cm⁻¹ band in its infrared spectrum.

EXAMPLE 8

The compound 7-(3′-chloro-4-fluorophenylthioacetamido)cephalosporanic acid, sodium salt was prepared by acylating 7-aminocephalosporanic acid with 3-chloro-4-fluorophenylmercaptoacetic acid substantially according to the procedure described in Example 1. The product has a maximum in its ultraviolet spectrum at 254 millimicrons (ε=10,400) and exhibited a 1760 cm⁻¹ band in its infrared absorption.

EXAMPLE 9

This example compares the antibiotic activities of three known compounds, methicillin, cephalothin, and cephaloridine, with three compounds from the above examples, in terms of minimum inhibitory concentration (MIC) values in microgram/milliliter units against various isolates of *Staphylococcus aureus* cultures. The culture numbers and the procedures used to obtain the reported data are disclosed by W. E. Wick and D. A. Preston in their article "Heterogeneous Methicillin-Resistant Staphylococcus Aureus" which appeared in *Progress in Antimicrobial And Anticancer Chemotherapy*, Proceedings of the 6th International Congress of Chemotherapy, Volume 1, U. of Tokyo Press, Tokyo (1970). In these agardilution susceptibility tests, the These data show that the compounds of Examples 1, 2 and 3 are substantially more effective than methicillin, cephalothin, and cephaloridine in in vitro tests against various cultures of methicillin-resistant *Staphylococcus aureus*.

EXAMPLE 10

This example compares the antibiotic activities of methicillin, cephalothin and cephaloridine with the compounds of Examples 1, 2 and 3, in broth dilution tests. The MIC values, in μg/ml., are against the same *Staphylococcus aureus* cultures described in Example 9, except that in this example the cultures were grown in trypticase soy broth (TSB). Growing the cultures in two broth cultures, one having a low (0.5 percent) sodium chloride content and one having a high (5.0 percent) sodium chloride content is said to assist in identifying the methicillin-resistant cultures from those which are not meticillin-resistant. There is a wide disparity in MIC values for methicillin in low versus high salt TSB cultures, which disparity or difference implies clinical resistance of these cultures to methicillin, but not with cultures susceptible to the antibiotic (e.g. 3055 and H232). See Chabbert, Y.A., 1967, *Postgrad. Med. J.*, 43 (suppl); 40-46. One expects that similar changes in MIC values for this type of culture to other β-lactam antibiotics, e.g., various penicillins and cephalosporins, to have similar implications. An example is cephalothin which shows fairly wide difference (increase in MIC value from 2 to 64) against some of these methicillin-resistant *Staphylococcus aureus* cultures. By the same line of reasoning, with the compounds used in the method of this invention this difference in MIC values does not appear. This suggests the absence of resistance in the heterogeneous population of the cultures to the antibiotic compounds used in the method of this invention. That is, methicillin-resistant *S. aureus* cultures are susceptible to the cephalosporin antibiotics used in this invention.

BROTH DILUTION MIC
PHENYLTHIOACETYL CEPHALOSPORINS vs METHICILLIN RESISTANT S. aureus
MIC (μg/ml) for Staphylococcus aureus cultures[a]

| Experiment Antibiotic | Controls | | | | | | | | | | | | | |
|---|---|---|---|---|---|---|---|---|---|---|---|---|---|---|
| | 3055 | H232 | 3130 | 3131 | 3132 | 3133 | 3134 | 3135 | 3136 | 3137 | 3138 | 3139 | (Seattle) 966 | Kavarnick 1138501 | S 35 | S 61 |
| Methicillin[b] | 2.0 | 4.0 | 16 | 16 | 32 | 8 | 32 | 32 | 32 | >128 | 128 | 16 | 8.0 | 32 | 16 | 16 |
| Cephalothin | 0.5 | 0.5 | 8 | 2.0 | 2.0 | 2.0 | 32 | 2.0 | 2.0 | 64 | 32 | 4.0 | 2.0 | 4.0 | 8 | 8 |
| Cephaloridine | ND | ND | ND | 2.0 | <.5 | 1.0 | ND | <.5 | <.5 | 8 | 4.0 | 1.0 | 4.0 | 2.0 | 4 | 4 |
| Example 3 | .06 | 0.12 | <.5 | <.5 | <.5 | <.5 | 1.0 | <.5 | 0.5 | 2.0 | 1.0 | 2.0 | 1.0 | 0.5 | 0.5 | 0.5 |
| Example 1 | .06 | 0.12 | 0.5 | 1.0 | <.5 | <.5 | 1.0 | <.5 | 0.5 | 2.0 | 1.0 | 1.0 | 0.5 | 0.5 | 2.0 | 2.0 |
| Example 2 | .06 | 0.12 | 1.0 | <.5 | <.5 | <.5 | 2.0 | <.5 | 0.25 | 2.0 | 2.0 | 0.5 | 0.5 | 0.5 | 0.5 | 0.5 |
| Methicillin[c] | 2.0 | 4.0 | 64 | 128 | 64 | 128 | 64 | 64 | 128 | >128 | 128 | >128 | 64 | 128 | 16 | 64 |
| Cephalothin | 0.5 | 0.5 | 64 | 64 | 64 | 64 | 64 | 64 | 64 | 128 | 64 | 32 | 32 | 64 | 64 | 64 |
| Cephaloridine | ND | ND | ND | 16 | 16 | 16 | ND | 16 | 16 | 32 | 16 | 8 | 8 | 16 | 16 | 16 |
| Example 3 | .06 | 0.12 | 2.0 | 1.0 | 1.0 | 2.0 | 2.0 | 2.0 | 2.0 | 4.0 | 2.0 | 2.0 | 8 | 1.0 | 2.0 | 1.0 |
| Example 1 | .06 | 0.25 | 4.0 | 2.0 | 2.0 | 2.0 | 4.0 | 2.0 | 2.0 | 4.0 | 1.0 | 1.0 | 2.0 | 2.0 | 2.0 | 2.0 |
| Example 2 | .06 | 0.25 | 8.0 | 2.0 | 2.0 | 2.0 | 4.0 | 2.0 | 4.0 | 4.0 | 2.0 | <0.5 | 2.0 | 2.0 | 2.0 | 2.0 |

Footnotes -
[a]Inocula of 10³ bacteria per ml. Cultures 3055 (benzylpenicillin-sensitive) and H232 (benzylpenicillin-resistant) are controls. The rest are methicillin-resistant, and except for 3136, are natural isolates. Culture 3136 is a 4th transfer mutant.
[b]TSB broth containing 0.5% sodium chloride.
[c]TSB broth containing 5.0% sodium chloride.

EXAMPLE 11

This example exemplifies the antibiotic activity of 7-[2'-(3"-chloro-4"-fluorophenylthio)acetamido]cephalosporanic acid, a water soluble compound, described in Example 8, against various *Staphylococcus aureus* cultures, in a modified Bauer-Kirby Disc Susceptibility Test (Bauer, A. W., W. M. M. Kirby, J. C. Sherris, and M. Turck, 1966, *Amer. J. Clin. Pathol.* 45:493–496). In this test the cultures were incubated at both 37° or 30° C. According to the suggestion of D. I. Annear in his article entitled "The Effect of Temperature on Resistance of *Staphylococcus aureus* to Methicillin and Some Other Antibiotics" in *The Medical Journal of Australia*, Mar. 16, 1968, the heterogeneity of methicillin-resistant *S. aureus* is manifested by incubation at 30° C. By this method, the soluble 7-[2'-(3"-chloro-4"-fluorophenylthio)acetamido]cephalosporanic acid (Example 8) appears more effective than cephalothin.

| | Bauer-Kirby Disc Susceptibility Test | | | | | | | | |
|---|---|---|---|---|---|---|---|---|---|
| | Example 8 | | | Example 3 | | | Cephalothin | | |
| S. aureus culture | 30 mg 37° | Disc 30° | Change 37°–30° (mm) | 30 mg 37° | Disc 30° | Change 37°–30° (mm) | 30 mg 37° | Disc 30° | Change 37°–30° (mm) |
| 3125* | 33.8 | 36.0 | +2.2 | 34.2 | 37.0 | +2.8 | 33.4 | 33.8 | + 0.4 |
| 3130* | 33.2 | 31.0 | −2.2 | 32.0 | 33.6 | +1.6 | 32.8 | 20.2 | −12.6 |
| 3131* | 26.6 | 29.0 | +2.4 | 30.6 | 31.8 | +1.2 | 29.6 | 16.6 | −13.0 |
| 3132* | 29.4 | 28.0 | −1.4 | 31.0 | 32.6 | +1.6 | 28.6 | 17.6 | −11.0 |
| 3133* | 27.6 | 24.8 | −2.8 | 29.0 | 30.8 | +1.8 | 28.8 | 12.8 | −16.0 |
| 3134* | 28.0 | 27.8 | −0.2 | 29.8 | 33.0 | +3.2 | 27.8 | 12.1 | −15.7 |
| 3135* | 28.2 | 26.2 | −2.0 | 28.3 | 29.6 | +1.3 | 28.0 | 11.8 | −16.2 |
| 3136* | 35.0 | 31.0 | −4.0 | 35.0 | 29.8 | +5.2 | 35.6 | 20.8 | −14.8 |
| 3137* | 24.4 | 22.1 | −2.3 | 26.2 | 26.0 | −0.2 | 17.8 | 0 | >17.8 |
| 3138* | 25.6 | 25.2 | −0.4 | 27.0 | 29.4 | +2.4 | 26.2 | 11.3 | −14.9 |
| 3139* | 34.0 | 31.6 | −2.4 | 36.0 | 32.2 | −3.8 | 32.0 | 27.0 | − 5.0 |
| 3140* | 28.4 | 26.4 | −2.0 | 28.8 | 30.2 | +1.4 | 29.7 | 10.4 | −13.3 |
| 3055** | >35 | >35 | — | >35 | >35 | — | >35 | >35 | — |
| 3074** | 36.0 | 36.0 | 0 | 35.0 | 35.0 | 0 | 31.8 | 32.1 | + 0.3 |
| H232** | 33.4 | 34.3 | +0.9 | 34.1 | 32.6 | −1.5 | 33.4 | 33.2 | − 0.2 |

Footnotes:
*3125-3140 Methicillin-resistant with varying degrees of resistance to cephalothin.
**3055-penicillin sensitive; 3074, H232-methicillin sensitive penicillinase producing.

EXAMPLE 12

The compound 7-[2'-(3"-chloro-4"-fluorophenylthio)acetamido]cephalosporanic acid, prepared as described in Example 8, was tested for antibiotic effectiveness against *Streptococcus pyogenes*, strain C203 infections in mice, and is compared with the effectiveness of cephaloridine in the same test. Experience has shown with other compounds, some of which are now commercial antibiotics, that a compound effective against *Streptococcus pyogenes*, strain C203 in this test will be effective against *Staphylococcus aureus* strains in clinical use. This is intended as further evidence that the compounds of the method of this invention should be effective antibiotics in clinical situations.

In this test, a standard in vivo test method described by Wick, W. E., F. Streightoff, and D. H. Holmes. 1961, in *J. Bacteriol.*, 81:233–235 was used. The oral and subcutaneous median effective doses ($ED_{50}$) necessary to cure 50 percent of the mice were calculated according to the method of Reed and Muench (Reed, L. J., and H. Muench. 1938. *Am. J. Hyg.* 27: 493–497) The results were as follows:

| Cephalosporin | Route | $ED_{50}$ (7g/kg × 2) | Infecting challenge ($XLD_{50}$) |
|---|---|---|---|
| Example 8 | Oral | 7 | 27.9 |
| | Subcut | <0.21 | 27.9 |
| Cephaloridine | Oral | 0.323 | 27.9 |
| | Subcut | 0.10 | 27.9 |

EXAMPLE 13

Synthesis of
7-[2-[(3-chloro-4-flurophenyl)thio]acetamido]-3-[[(5-methyl-1,3,4-thiadiazol-2-yl)thio]methyl]-3-cephem-4-carboxylic acid, sodium salt 3-Chloro-4-fluorophenylthioacetic acid, 2.20 g. (10 mM) was dissolved in dry benzene (50ml.) and 10 ml. of oxalyl chloride and 1 drop DMF was added to the solution. The reaction mixture was stirred 1 hour at 25° C. The benzene and excess oxalyl chloride were then removed in vacuo to yield the acid chloride as a yellowish syrup. This syrup was taken up in benzene and again reduced in vacuo two times to remove any residual oxalyl chloride and HCl. This syrup was then taken up in 20 ml. dry acetone and added dropwise to a stirred solution of 7-amino-3-(5-methyl-1,3,4-thiadiazol-2-yl thio methyl)-3-cephem-4-carboxylic acid, 3.44 g. (10 mM); sodium bicarbonate, 3.44 g.; 50 ml. $H_2O$ and 50 ml. acetone at −10° C. The reaction mixture was stirred at ice bath temperatures for 1 hour. The acetone was removed in vacuo and the aqueous portion layered with 50 ml. of ethyl acetate. The mixture was acidified to pH 2 with HCl. The aqueous portion re-extracted with 30 ml. ethyl acetate. The organic layers were combined and dried over $MgSO_4$, filtered, and reduced in vacuo to yield a yellow syrup. This was taken up in ethanol and sodium 2-ethyl hexanoate (3.4 mM) added, whereupon crystals of the product appeared. The solid was filtered, washed with ethanol and dried in vacuo. The product exhibited a 1760 cm$^{-1}$ band in the infrared spectrum (β-lactam) and had an ultraviolet spectrum of 270 mμ ($\epsilon$ = 14,200). All other physical data were consistent with the proposed structure. The compound is soluble in water at concentrations greater than 100 mg./milliliter of solution at room temperature. Upon warming the solubility of the compound increases.

The compound, 7-[2-[(3-chloro-4-fluorophenyl)thio]acetamido]-3-[[(5-methyl-1,3,4-thiadiazol-2-yl)thio]methyl]-3-cephem-4-carboxylic acid, sodium salt was tested for its antibiotic effectiveness against the same *Staphylococcus aureus* cultures described in Example 9. The table which follows gives the minimum inhibitory concentration (MIC) in micrograms of compound per milliliter of culture (μg/ml), in comparison with similar MIC values for the known antibiotics methicillin, cephalothin and cephaloridine against the same strains of bacteria.

The compound of Example 13 gave the following in vitro minimum inhibitory concentrations (MIC values), in microgram/milliliter of agar (μg/ml.) against the following additional microorganisms

| Organism | MIC (μg/ml.) |
| --- | --- |
| S. aureus, 3055 (penicillin G susceptible) | 0.031 |
| S. aureus 3074 (Pen G. resist.) | 0.062 |
| S. facalis X66 | 400 |
| P. morganii, indole positive | >128 |
| S. typhosa SA12 | 32 |
| H. pneumoniae KL14 | 64 |
| E. aerogenes EB17 | 128 |
| E. coli EC14 | 64 |
| C. freundii CF17 | >128 |
| P. aeroginosa X239 | >128 |
| S. marcescens SE3 | >128 |
| S. typhimurium | 128 |
| B. bronchiseptica | >128 |
| P. solenaecarum X185 | >128 |
| E. amylovora | 64 |
| C. tropicalis A17 | >128 |
| T. mentagrophytes 27 | >128 |
| A. flavus | >128 |
| C. ulmi | >128 |

The MIC for the compound of Example 13 against *Streptococcus pyogenes* C203 in broth was 0.008 μg/ml. The *S. pyogenes* subcutaneous median effective dose ($ED_{50}$ value) was 0.281 μg/ml against a challenge dose of 1260 $LD_{50}$ of the bacteria.

I claim:
1. A cephalosporin antibiotic compound of the formula in which
R' is hydrogen, dicyclohexylamine, or a pharmaceutically acceptable cation;
R is selected from the group consisting of hydrogen, $C_1$ to $C_4$-alkanoyloxy, and N-pyridino;
and X and Y are chlorine and are in the 3,4-, the 3,5-, or the 2,5-positons.

2. Compound of claim 1, in which R is other than $C_1$ to $C_4$ alkanoyloxy.

3. Compound of claim 2, in which X and Y are in the 2,5-positions.

4. Compound of claim 1, in which R is acetoxy.

5. Compound of claim 4, in which the phenyl ring is substituted with chlorines in the 2- and 5- positions.

* * * * *

UNITED STATES PATENT AND TRADEMARK OFFICE
CERTIFICATE OF CORRECTION

PATENT NO. : 4,056,676
DATED : November 1, 1977
INVENTOR(S) : George W. Huffman

It is certified that error appears in the above-identified patent and that said Letters Patent are hereby corrected as shown below:

Column 5, line 5, "2,4-dichloro-5-fluorophenyl," should be deleted.

Column 7, line 15, "3-(1'H-" should read --3-(1'-methyl-1'H- --.

Column 8, line 13, "-3cephem-" should read -- -3-cephem- --.

Column 8, line 29, "-5''-flurorphenylthi-" should read -- -5''-fluorophenylthi- --.

Column 8, line 32, "-4carboxy- -- should read -- -4-carboxy- --.

Column 12, line 47, "meticillin-" should read --methicillin- --.

Column 13, in the table, line should be inserted after "Example 2" to extend the length of the table and immediately before "Methicillin$^c$".

Column 15, line 44, "pyrogenes," should read --pyogenes,--.

Column 16, line 4, "-4-flurophenyl)" should read -- -4-fluorophenyl)--.

UNITED STATES PATENT AND TRADEMARK OFFICE
CERTIFICATE OF CORRECTION

PATENT NO. : 4,056,676
DATED : November 1, 1977
INVENTOR(S) : George W. Huffman

It is certified that error appears in the above-identified patent and that said Letters Patent are hereby corrected as shown below:

Column 17, the following heading was omitted from the table:

Agar Dilution MIC
Example 13 Compound vs. Methicillin Resistant <u>Staphylococcus aureus</u>

MIC(μg/ml) for <u>S</u>. <u>aureus</u> cultures

Controls

In this same table a line should be inserted to extend the entire length of the table following Example 13 and before Methicillin.

Signed and Sealed this

First Day of August 1978

[SEAL]

Attest:

RUTH C. MASON
Attesting Officer

DONALD W. BANNER
Commissioner of Patents and Trademarks